United States Patent
Albrektsson et al.

[11] Patent Number: 5,817,098
[45] Date of Patent: Oct. 6, 1998

[54] DRILL GUIDE INSTRUMENT

[75] Inventors: Björn Albrektsson, Onsala; Lars Carlsson, Kullavik; Magnus Jacobsson, Göteborg; Tord Röstlund, Kullavik; Stig Wennberg, Angered, all of Sweden

[73] Assignee: Astra Aktiebolag, Sodertalje, Sweden

[21] Appl. No.: 669,474
[22] PCT Filed: Apr. 17, 1996
[86] PCT No.: PCT/SE96/00490
§ 371 Date: Jul. 9, 1996
§ 102(e) Date: Jul. 9, 1996
[87] PCT Pub. No.: WO96/36285
PCT Pub. Date: Nov. 21, 1996

[30] Foreign Application Priority Data

May 17, 1995 [SE] Sweden ................................. 9501829

[51] Int. Cl.[6] .................................................. A61B 17/17
[52] U.S. Cl. ............................... 606/96; 606/80; 606/89; 606/205
[58] Field of Search .................. 606/65, 66, 67, 606/68, 80, 89, 96, 88, 87, 86; 623/22, 23

[56] References Cited

U.S. PATENT DOCUMENTS 5,417,695   5/1995   Axelson, Jr. ............................. 606/89

FOREIGN PATENT DOCUMENTS

| 0243109 | 10/1987 | European Pat. Off. . |
| 1644-933-A | 4/1991 | U.S.S.R. . |
| 8911837 | 12/1989 | WIPO . |
| 9301769 | 2/1993 | WIPO . |
| 9316663 | 9/1993 | WIPO . |

*Primary Examiner*—Michael Powell Buiz
*Assistant Examiner*—David O. Reip
*Attorney, Agent, or Firm*—White & Case L.L.P.

[57] ABSTRACT

The invention relates to a drill guide instrument and method for guiding a drill tool (24) when drilling a longitudinal bore (4) through the neck (collum femoris) (5) of a human femur (9), subsequent to resection of the head (caput) (8) of the collum (5) along a cutting plane (P). The instrument comprises a drill guide (20), which is provided with a base member (21) and arranged to guide the drill tool (24) along a drill axis (B—B) relative to the base member (21), said base member (21) being intended to be applied against a cut end surface (11) of the collum (5) defining the cutting plane (P) for obtaining a predetermined orientation of the drill axis (B—B) relative to the cutting plane (P). A positioning member (22) extending from the drill guide (20) is intended to be contacted with the periphery of the narrowest portion (13) of the collum (5) in at least two circumferentially-spaced contact positions (30), so as to locate the drill axis (B—B) at a minimum distance from the periphery of said narrowest portion (13) of the collum (5). The invention also relates to the use of the instrument for performing such drilling.

20 Claims, 4 Drawing Sheets

DRILL GUIDE INSTRUMENT

TECHNICAL FIELD OF THE INVENTION

The invention relates to the field of hip joint prostheses for permanent anchorage in the human hip joint. More specifically, the invention relates to a drill guide instrument for guiding a drill tool when drilling a longitudinal bore through the neck (collum femoris) of the human femur, subsequent to a resection of the head (caput) of the collum. The invention also relates to the use of such an instrument, as well as a method for drilling such a bore.

BACKGROUND ART

The invention being especially, but not exclusively, applicable to the anchorage of hip joint prostheses of the type disclosed in WO 93/16663, the technical background to the invention will be described with specific reference to this document and the problems encountered when mounting a hip joint prosthesis of the type disclosed therein. However, the invention is applicable also to other types of hip joint prostheses.

WO 93/16663 discloses a hip joint prosthesis comprising an attachment part for a ball unit designed to be anchored in the neck of the human femur (collum femoris). The attachment part comprises a part for carrying a ball or caput intended to be attached to the collum after a resection of the head of the collum has been performed. The attachment part also comprises a fixture member having two main parts, namely a first part which is to extend through a bore extending from the collum towards the outer side of the femur, and a plug-like second part intended to fit into a cylindrical recess cut in the cancellous bone of the collum. A hip joint prosthesis of this kind is illustrated in FIG. 1 of the accompanying drawings. Further examples of prior-art hip joint prostheses are disclosed in WO 93/01769 and WO 89/11837.

In order to obtain a strong anchorage of the prosthesis, the plug-like second fixture part may be brought into engagement with the inside of the cortical bone in the collum, as discussed in general terms in WO 93/16663, since a direct contact with the cortical bone will reduce the risk of mechanical loosening of the prosthesis. However, any perforation of the cortical bone of the collum must be avoided, as discussed in the same document. Especially, the cortical bone must not be perforated by the cylindrical recess or by the plug-like part received therein. Since the cylindrical recess is concentric with the drilled bore and actually is cut in the collum with the aid of the drilled bore as guide channel, the longitudinal bore must be drilled through the collum along an axis having a predetermined orientation and a predetermined position relative to the collum in order to obtain the aimed-at engagement between the plug-like fixture part and the cortical bone.

It is, therefore, an object of the invention to enable high-precision drilling of a longitudinal bore through the collum of the human femur along a drill axis having a predetermined orientation and a predetermined position relative to the collum.

It is also an object of the invention to enable expedient and reliable high-precision drilling of this type.

Especially, it is an object of the invention to orient and position the drill axis in such a way that a hip joint prosthesis subsequently anchored in the collum will firmly engage the cortical bone of the collum, while reducing the risk of any perforation of the cortical bone.

A particular object of the invention is to provide a drill guide instrument by means of which both the orientation and the position of the drill axis relative to the collum can be determined in a reliable and accurate manner, and which can be used for guiding a drill tool or the equivalent along the drill axis thus established.

DISCLOSURE OF THE INVENTION

These and other objects of the invention are achieved by a drill guide instrument and method, as well as the use of such an instrument, having the features set out in the appended claims.

Thus, a drill guide instrument according to the invention comprises a drill guide provided with a base member and arranged to guide the drill tool along a drill axis relative to the base member, said base member being intended to be applied against a cut end surface of the collum defining a cutting plane, along which the head (caput) of the collum has been removed, for obtaining a predetermined orientation of the drill axis relative to the cutting plane. The instrument further comprises a positioning member, which extends from the drill guide and is intended to be contacted with the periphery of the narrowest portion of the collum in at least two circumferentially-spaced contact positions, so as to locate the drill axis at a minimum distance from the periphery of the narrowest portion of the collum.

With the aid of the instrument according to the invention, a bore for receiving a fixture member of a hip joint prosthesis can be drilled longitudinally through the femoral collum along a drill axis having the correct orientation as well as the correct position relative to the collum.

The instrument according to the invention is to be used subsequent to a resection of the head (caput) of the collum along a cutting plane, the instrument using this cutting plane as reference plane in order to establish the correct orientation of the drill axis relative to the collum. Accordingly, the base member of the drill guide serves to orient the guide, i.e. the drill axis, relative to the cut end surface of the collum. In a preferred embodiment of the invention, the drill axis is orientated at right angles to the cutting plane. Since the drill guide instrument uses the cutting plane as reference plane, the resection of the head of the collum should preferably be exactly performed at predetermined angles to the longitudinal extension of the collum. The Swedish patent application SE 9501828-9, entitled "cutting guide instrument", discloses a cutting guide instrument suitable for this purpose.

In the preferred embodiment of the instrument, the drill guide is provided with a guide channel for receiving and guiding the drill tool along a longitudinal axis of the drill channel coinciding with the drill axis. However, the statement that the drill guide being intended to guide a drill tool along a drill axis relative to the base member is meant to encompass not only the alternative of the drill tool being separate from the instrument of the invention, as will be described below with reference to the preferred embodiment of the instrument, but also the alternative of the drill tool being an integral part of the instrument. Thus, the drill guide may also comprise a jig for supporting the drill tool and guiding it relative to the base member.

In order to establish also the correct position of the drill axis relative to the collum, especially a position resulting in a firm engagement between the fixture part of the prosthesis and the cortical bone without any perforation of the latter, the instrument according to the invention comprises the above-mentioned positioning member which, in use, extends from the drill guide, beyond the cutting plane and towards the collum, so as to abut against the periphery of the narrowest portion of the collum in at least two circumferentially-spaced contact positions. As a result, the drill axis can be positioned at a predetermined minimum distance from the periphery of the narrowest portion of the collum. In the preferred embodiment of the invention, the positioning member is intended to be brought into simultaneous abutment against the collum in said contact positions. However, the positioning member may also be arranged to be brought into abutment in only one contact position at a time.

It is preferred that the positioning member is detachably connected to the instrument, so as to be replaceable with other positioning members corresponding to different values of the minimum distance mentioned above. This embodiment is advantageous in that one and the same drill guide can be used for different-sized femoral colla. In this embodiment, the minimum distance is first determined by measuring the size of the narrowest portion of the collum. Then, a positioning member corresponding to the minimum distance thus determined will be selected from a set of different positioning members and mounted on the instrument.

It is also preferred that the positioning member be displaceable relative to the base member transversely of the cutting plane, in order to allow for an adjustment of the positioning member to a position in which the portions of the positioning member that are to abut against the periphery of the collum are on a level with the narrowest portion thereof.

Furthermore, the instrument according to the invention preferably comprises means for temporarily fixing the base member relative to the collum. Considering that the cutting plane is to be used as reference plane for the base member, such fixing means may advantageously be adapted to clamp the base member against the cut end surface of the collum defining the cutting plane.

A method according to the invention for drilling a longitudinal bore through the neck (collum femoris) of the human femur, subsequent to a resection of the head (caput) of the collum along a cutting plane, is characterised by the steps of:

applying a drill guide instrument against a cut end surface of the collum defining said cutting plane, using said cut end surface as a reference plane for bringing a drill axis of said drill guide instrument into a predetermined orientation relative to said cutting plane, and using at least two circumferentially-spaced positions of the periphery of the narrowest portion of the collum as reference positions for locating said drill axis at a minimum distance from said periphery of said narrowest portion of the collum, and drilling said longitudinal bore by means of a drill tool guided by the thus-applied drill guide instrument along the orientated and located drill axis.

Preferred modes of implementation of the inventive method are set out in the dependent claims.

DETAILED DESCRIPTION OF A PREFERRED EMBODIMENT OF THE INVENTION

Figure 1:
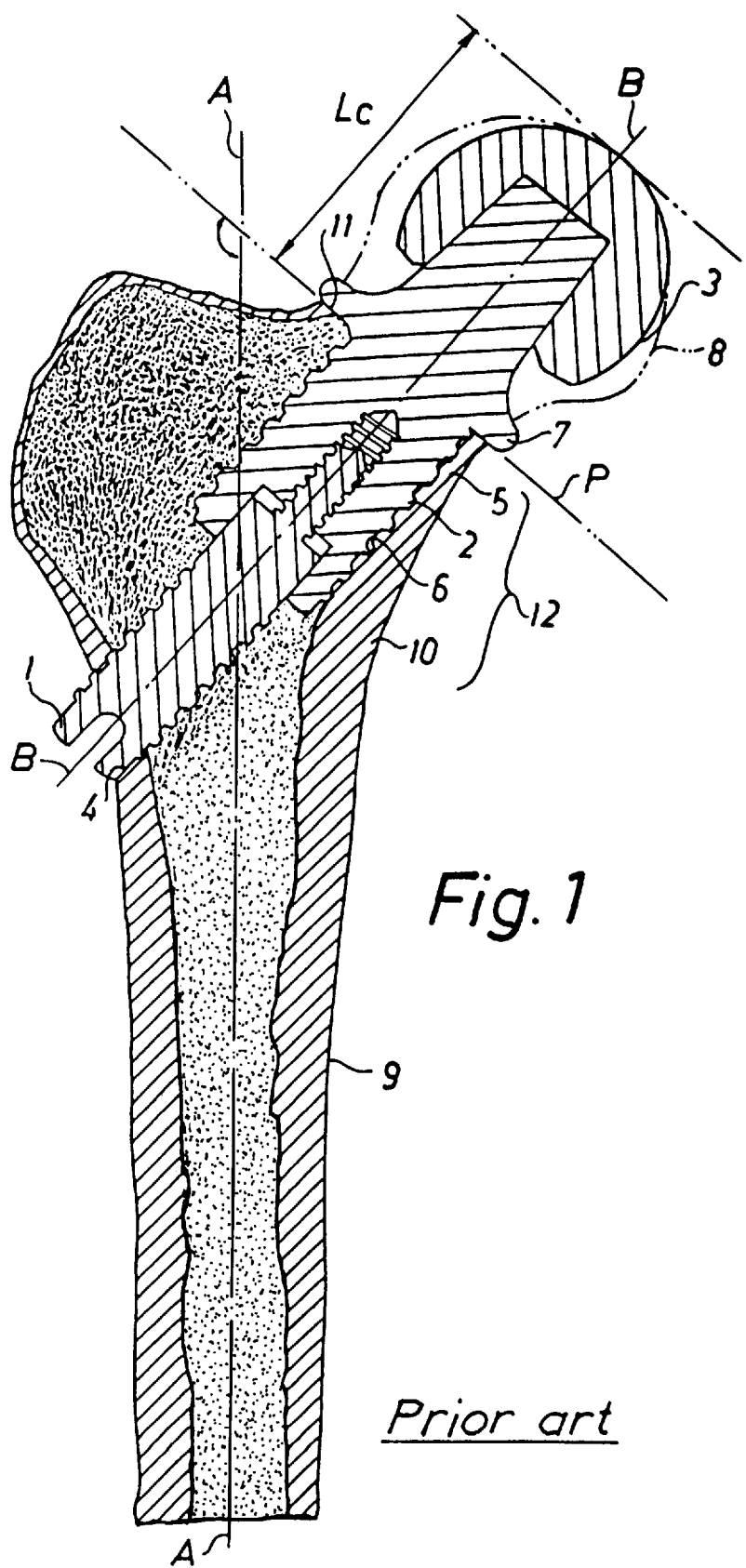
FIG. 1 is a sectional view of a prior-art hip joint prosthesis anchored in the collum of a human femur along a drilled bore.

In order to illustrate the advantages of the present invention, reference is first made to FIG. 1, which illustrates a hip joint prosthesis of the type disclosed in WO93/16663. The prosthesis comprises a cylindrical first fixture part 1, and a plug-like second fixture part 2 carrying a ball or caput 3. The first fixture part 1 is made in several versions of different length, whereas the plug-like second fixture part 2 is made in several versions of different diameter.

The first fixture part 1 has been fitted into a bore 4, which has been drilled longitudinally through the cancellous bone of the femoral collum 5 along a drill axis B—B by means of a drill tool (reference numeral 24 in FIG. 2) having a diameter corresponding to that of the first fixture part 1. The plug-like, second fixture part 2 has been fitted into a cylindrical recess 6 cut in the cancellous bone of the collum 5 so as to be coaxial with the drilled bore 4. The cylindrical recess 6 has been cut longitudinally along the drill axis B—B in a direction away from the head 8 by means of a rotary milling tool (not shown). The milling tool is available in several sizes, each corresponding to a specific diameter of a plug-like, second fixture part 2, and comprises an elongate guide element to be inserted in and guided by the drilled bore 4.

The plug-like, second fixture part 2 is delimited by a circumferential flange 7 limiting the insertion into the recess 6, the flange 7 abutting against a cut end surface 11 which defines a cutting plane P, along which the head 8 of the collum 5 has been removed. Reference is made to WO93/16663 for further details of this prior-art prosthesis shown in FIG. 1 and the anchorage thereof.

In FIG. 1, the orientation of the fixture parts 1 and 2 relative to the collum 5, and especially the cortical bone 10, differs from what has previously been disclosed in WO93/16663. More specifically, the plug-like, second fixture part 2 firmly engages, along its entire length, the cortical bone 10 in a specific area 12 located along the medial aspect of the transition zone between the femoral collum 5 and the femoral shaft 9. Since the overall object is to maximize the support for the fixture part 1, 2 without penetrating the cortical bone 10, the area 12 of the cortical bone 10, which is relatively thick as illustrated in FIG. 1, is advantageously used for engaging and supporting the plug-like, second fixture part 2.

Thus, in order to ensure strong anchorage of the prosthesis, both the orientation and the position of the drill axis B—B are preferably established with a high degree of accuracy during the drilling operation, since the bore 4 is subsequently used as guide channel for the milling tool when cutting the recess 6 in the cancellous bone of the collum 5, as stated above. Should the orientation and/or the position of the drill axis B—B be incorrect during the drilling of the bore 4, the cylindrical periphery of the cut recess 6 will either (i) be entirely or partly spaced from the advantageous area 12 of the cortical bone 10, resulting in no or only partial anchorage of the plug-like, second fixture part 2 in the cortical bone 10, especially in the advantageous area 12, or (ii) be displaced towards the cortical bone to such an extent that the latter is penetrated, either by the recess 6 or by the plug-like, second fixture part 2.

Figure 3:
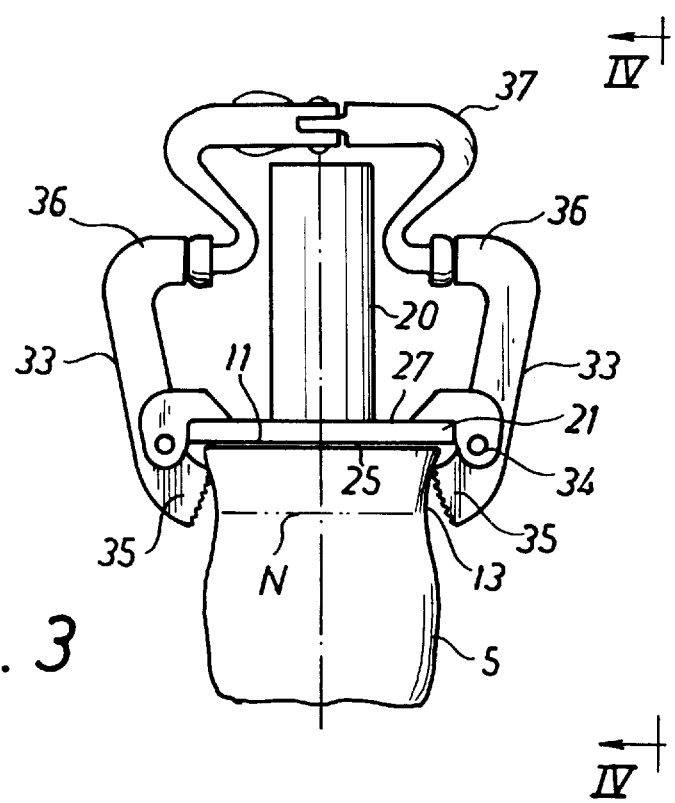
FIG. 3 is a lateral end view taken along the line III—III in FIG. 2, a positioning member of the instrument having been removed for the sake of clarity.

As to the risk of penetrating the cortical bone, the situation is complicated due to the fact that the collum 5 is normally funnel-shaped adjacent to the cutting plane P, as most clearly illustrated in FIG. 3, in which a dashed line N indicates the narrowest part 13 of the collum 5. Due to the funnel-shape of the collum 5, correct positioning of the drill axis B—B relative to the collum 5, i.e. correct positioning of the point of intersection of the drill axis B-B and the cutting plane P, cannot be determined on the basis of the profile section of the cut end surface 11, since it is the size of the narrowest part 13 that determines the maximum permissible size of the milling tool to be used, and hence the maximum permissible diameter of the plug-like, second fixture part 2.

In FIG. 1, the cutting plane P has been so chosen as to make a predetermined cutting angle $\alpha_c$ with the femoral shaft 9, the longitudinal main direction of which is identified by a straight line A—A, and be located at a predetermined cutting level $L_c$ with respect to the end of the head 8. Resection of the head 8 along such a well-defined cutting plane may preferably be performed by means of a cutting guide instrument as disclosed in the above-mentioned SE 9501828-9.

Figure 2:
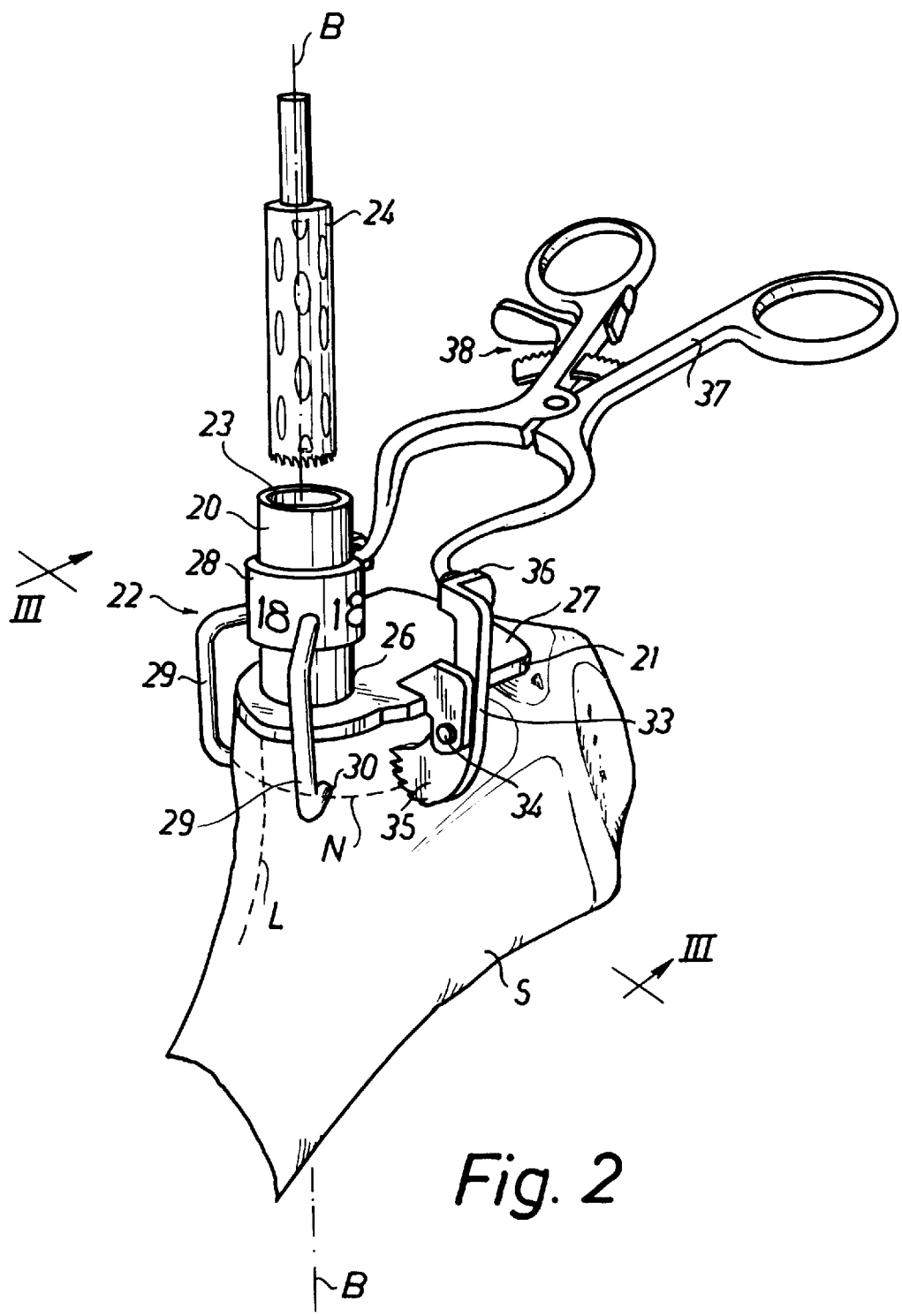
FIG. 2 is a perspective view of a preferred embodiment of the drill guide instrument according to the invention, which is mounted in drill guide position on a cut end surface of a femoral collum.
Figure 4:
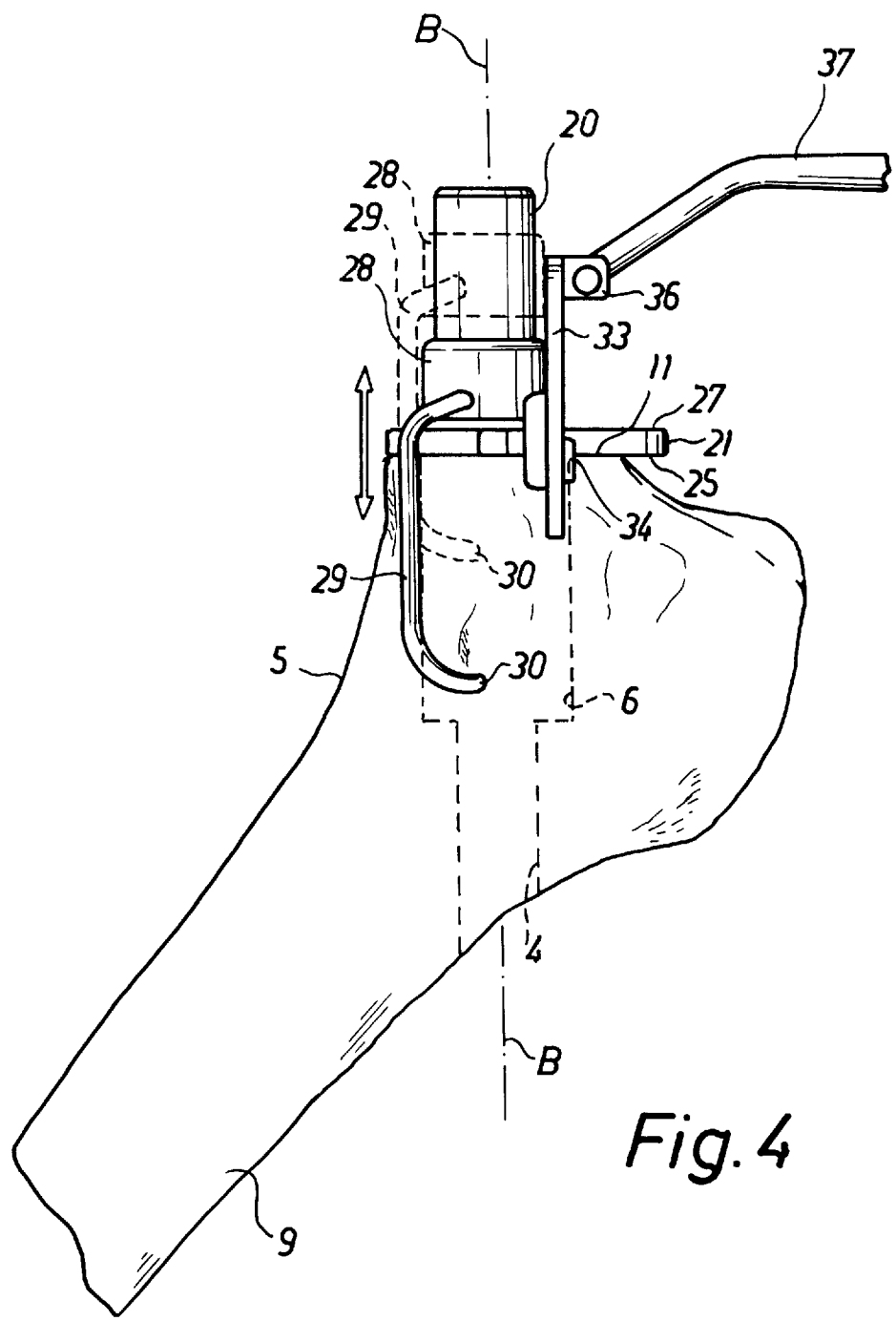
FIG. 4 is a lateral side view taken along the line IV—IV in FIG. 3, including the positioning member.

Referring now to FIGS. 2–4, the structure and the use of the preferred embodiment of the drill guide instrument according to the invention will be described below, like parts in FIG. 1 and FIGS. 2–4 bearing like reference numerals.

Generally, the instrument according to the invention comprises a drill guide 20 having a base member 21 and a positioning member 22 connected to the drill guide 20. In the preferred embodiment shown, the drill guide 20 is in the form of a tubular cylinder, the inner periphery of which defines a guide channel 23 for receiving and guiding a drill tool 24 along the drill axis B—B. In FIG. 2, the drill tool 24 is a trephine, but any other drill tool may also be used. The base member 21 of the drill guide 20 is in the form of a plate having an plane abutment surface 25 covering essentially the entire cut end surface 11. One end 26 of the cylinder 20 is fixedly connected at right angles to the opposite surface 27 of the abutment plate 21, which is provided with a through hole (not shown) coinciding with the guide channel 23 of the cylinder 20.

The positioning member 22 is an exchangeable part of the drill guide instrument and comprises a cylindrical connection sleeve 28, which fits loosely over the cylinder 20 and is provided with two essentially U-shaped positioning arms 29. In use, the positioning arms 29 extend from the connection sleeve 28, beyond the base plate 21 and towards the collum 5, as shown in FIGS. 2 and 4. The U-shaped positioning arms 29 are essentially orthogonal and extend in respective radial planes of the drill axis B-B. The distal ends of the positioning arms 29 form abutment ends 30, both of which are to be brought into contact with the periphery of the collum 5 at the narrowest portion 13 thereof, as indicated by the dashed line N in FIG. 2.

Figure 5:
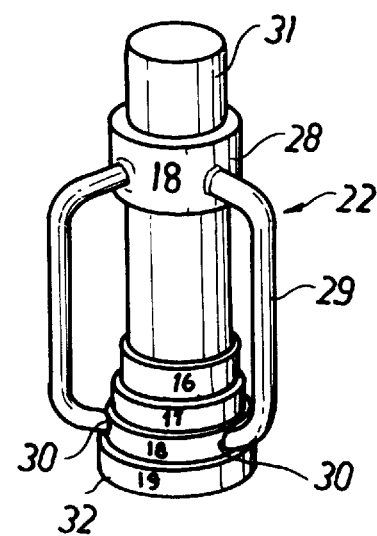
FIG. 5 is a perspective view of a testing and control device for use in association with the instrument shown in FIGS. 2–4.

The preferred embodiment of the instrument comprises a set of exchangeable positioning members 22, each having a connection sleeve 28 with two positioning arms 29. The positioning members 22 of the set differ only in radial distance, as measured from their abutment ends 30 to the centre axis of the connection sleeve 28. In other words, the two abutment ends 30 and the centre axis of the connection sleeve 28 define circles of different diameters for each of the positioning members 22 of the set. As an example, such a set may comprise four different positioning members 22, corresponding to diameters of 16 mm, 17 mm, 18 mm and 19 mm. FIG. 5 illustrates a control device comprising a cylindrical shaft 31 and a stepped conical base 32 and adapted to verify that the abutment ends 30 of each positioning member 22 of such a four-member set are located at the correct distance from the centre axis of the connection sleeve 28.

FIGS. 2 and 3 illustrate a situation in which a positioning member 22 of size "18" (diameter=18 mm) has been selected, after the size of the narrowest portion 13 of the collum 5 had been measured at N to be about 24 mm. In order to obtain, say, a 3-mm safety margin for the thickness of the cortical bone 10 at the narrowest portion 13 of the collum, the diameter of the plug-like, second fixture part 2 10 should be selected to be 18 mm. Thus, by selecting a positioning member 22 of size "18", the drill axis B—B will be located at a minimum distance of 18 mm/2=9 mm from the outer periphery of the narrowest portion 13 of the collum 5. In this example, the recess 6 for the plug-like fixture part 2 may be cut with a milling tool having a diameter of 18 mm or slightly less, depending on whether the plug-like, second fixture part 2 will remove any further bone tissue when inserted in the recess 6.

In the preferred embodiment of FIGS. 2–4, the base plate 21 is clamped against the cut end surface 11 of the collum 5 by means of two pivotable jaws 33. As illustrated most clearly in FIG. 3, each jaw is pivotably connected to the base plate 21 at 34 for pivotal movement in a plane perpendicular to the base plate 21. The jaws 33 comprise co-operating, toothed engagement ends 35, which can be clamped against the collum 5 by forcing apart the opposite ends 36 with the aid of a separate hand-held clamping tool 37 having conventional means 38 for locking the tool in a clamped position. The above-mentioned funnel shape of the collum 5 in combination with the pivotal movement of the jaws 33 will also effect clamping of the 30 base plate 21 downwards in FIG. 3 against the cut end surface 11, in order to ensure correct orientation of the cylinder 21 relative to the cutting plane P.

The following steps are to be taken when using the above drill guide instrument. After resection of the head 8 from the collum 5, the size of the narrowest portion 13 of the collum 5 is measured. The position of the narrowest portion 13 may be marked by a line (N). Based on this measurement, a positioning member 22 corresponding to a convenient size of the plug-like, second fixture part 2 is selected for mounting on the cylinder 20. Thereafter, the abutment surface 25 of the base plate 21 is brought into engagement with the cut end surface 11 of the collum 5. The positioning member is manually displaced along the cylinder 20 from the base plate 21, as illustrated in FIG. 4, to a position in which the abutment ends 30 of the positioning arms 29 are on a level (at line N) with the narrowest portion 13. However, the indication line can be dispensed with, since the narrowest portion 13 of the collum may easily be located by displacing the positioning member 22 along the cylinder 20 while constantly urging the two abutment ends 30 into contact with the periphery of the collum. Preferably, the connection sleeve 28 is rotated about the cylinder 20 to an angular position in which the abutment ends 30 of the arms 39 are at equal angular distance from a plane of symmetry of the collum, as indicated by a dashed line L in FIG. 2. The drill axis B—B being now correctly orientated and positioned, the whole instrument is temporarily fixed to the collum 5 by means of the jaws 33 and the clamping tool 37. The drill tool 24 can now be received in and guided by the drill channel 23 for drilling the bore 4 longitudinally through the collum 5, whereupon the drill guide instrument is removed. Finally, the recess 6 is cut in the cancellous bone as described above, using the drilled bore 4 as guide channel for a milling tool.

Several modifications of the embodiment described above are conceivable within the scope of the appended claims. For example, the drill guide may be formed by a number of coaxial rings forming a guide channel for a drill tool. Furthermore, the drill tool may be formed integral with the instrument, and in that case the structure of the drill guide may differ essentially from that of the embodiment shown in the Figures. In a more simple embodiment, the positioning member may be fixedly connected to the drill guide. As to the base member, other alternatives than a plate could be envisaged, e.g. some form of tripod arrangement for orienting the drill guide relative to the cut end surface. Finally, the abutment ends 30 of the positioning member could be in the form of a continuous ring abutting against the collum along the line N.

We claim:

1. A drill guide instrument for guiding a drill tool when drilling a longitudinal bore through the femoral collum of a human femur, subsequent to resection of the head (caput) of the collum along a cutting plane, said collum having a narrowest portion, said instrument comprising:

a drill guide provided with a base member and arranged to guide the drill tool along a drill axis relative to the base member, said base member being intended to be applied against a cut end surface of the collum defining the cutting plane for obtaining a predetermined orientation of the drill axis relative to the cutting plane; and a positioning member, which extends from the drill guide and is intended to be contacted with the periphery of the narrowest portion of the collum in at least two circumferentially-spaced contact positions, so as to locate the drill axis at a minimum distance from the periphery of said narrowest portion of the collum.

2. An instrument according to claim 1, wherein said positioning member is detachably connected to the instrument, so as to be replaceable with other positioning members corresponding to different values of said minimum distance.

3. An instrument according to claim 1, wherein the drill guide is provided with a drill channel for receiving and guiding the drill tool along the drill axis.

4. An instrument according to claim 3, wherein the drill guide comprises a tubular member, which is connected at one end to the base member and which has an inner cylindrical surface which defines the guide channel, and an outer cylindrical surface along which a connection sleeve of the positioning member is displaceable.

5. An instrument according to claim 1, wherein the positioning member is displaceable relative to the base member transversely of the cutting plane.

6. An instrument according to claim 1, wherein the positioning member is rotatable about the drill axis.

7. An instrument according to claim 1, wherein the base member has a plane abutment surface of sufficient dimensions to cover at least a major part of the cut end surface of the collum defining the cutting plane.

8. An instrument according to claim 1, wherein the drill axis is orientated at right angles to the base member.

9. An instrument according to claim 1, further comprising means for fixing the base member relative to the collum.

10. An instrument according to claim 9, wherein the fixing means comprises at least two jaws hingedly connected to the base member so as to pivot transversely of the cutting plane in order to be clamped against the outer periphery of the collum.

11. An instrument according to claim 10, wherein the jaws are hingedly connected to the base member in such a way that, when clamped against the collum, they press the base member against the cut end surface of the collum.

12. The use of an instrument according to claim 1 for drilling a longitudinal bore through the femoral collum of the human femur in order to anchor a hip-joint prosthesis in said bore, wherein:

the head (caput) of the collum is removed along a cutting plane, defining a cut end surface of the collum, the base member of the drill guide is applied against said cut end surface for obtaining a predetermined orientation of the drill axis relative to the cutting plane, the positioning member is brought into contact with the periphery of the narrowest portion of the collum in at least two circumferentially-spaced contact positions, so as to locate the drill axis at a minimum distance from the periphery of said narrowest portion of the collum, and the longitudinal bore is drilled by means of a drill tool guided by the thus-applied drill guide along the orientated and located drill axis.

13. A method for drilling a longitudinal bore through the femoral collum of the human femur, subsequent to a resection of the head (caput) of the collum along a cutting plane, said collum having a narrowest portion, said method comprising:

applying a drill guide instrument against a cut end surface of the collum defining said cutting plane, using said cut end surface as a reference plane for bringing a drill axis of said drill guide instrument into a predetermined orientation relative to said cutting plane, and using at least two circumferentially-spaced positions of the periphery of the narrowest portion of the collum as reference positions for locating said drill axis at a minimum distance from said periphery of said narrowest portion of the collum; and drilling said longitudinal bore by means of a drill tool guided by the thus-applied drill guide instrument along the orientated and located drill axis.

14. A method according to claim 13, further comprising the step of fixing the drill guide instrument relative to the cutting plane prior to the step of drilling the longitudinal bore.

15. A method according to claim 14, wherein said fixing step comprises the substep of pressing the drill guide instrument against the cut end surface of the collum.

16. A method according to claim 13, wherein said drill guide instrument comprises a base member and a guide member connected thereto, the base member being applied against the cut end surface and the drill tool being guided through an internal guide channel of the guide member during said drilling step.

17. A method according to claim 13, wherein the drill axis is orientated at right angles to the cut end surface.

18. A method according to claim 13, wherein said step of using at least two circumferentially-spaced positions of the periphery of the narrowest portion of the collum as reference positions for locating the drill axis at a minimum distance from the periphery of said narrowest portion of the collum, comprises the substep of bringing a positioning member of the drill guide instrument into contact with the periphery in said at least two circumferentially-spaced positions.

19. A method according to claim 18, wherein said step of bringing the positioning member into contact with the periphery of the collum comprises the substep of displacing the positioning member relative to the cut end surface in order to locate said narrowest portion of the collum.

20. A method according to claim 18, wherein said positioning member is detachably connected to the instrument, said method further comprising, prior to the step of bringing the positioning member into contact with the periphery of the collum, the step of determining said minimum distance by measuring the size of said narrowest portion of the collum, and the step of selecting, based on said measurement, said positioning member from a set of different positioning members corresponding to different sizes of said narrowest portion of the collum.

* * * * *